(12) United States Patent
Widmer

(10) Patent No.: US 6,976,397 B2
(45) Date of Patent: Dec. 20, 2005

(54) MULTI-POINT SAMPLING METHOD FOR OBTAINING ISOKINETIC FLUID COMPOSITION FLOWS IN A NON-UNIFORM VELOCITY FLOW FIELD

(75) Inventor: Neil Colin Widmer, Irvine, CA (US)

(73) Assignee: General Electric Company, Shenectady, NY (US)

( * ) Notice: Subject to any disclaimer, the term of this patent is extended or adjusted under 35 U.S.C. 154(b) by 38 days.

(21) Appl. No.: 10/605,795

(22) Filed: Oct. 28, 2003

(65) Prior Publication Data

US 2005/0087028 A1  Apr. 28, 2005

(51) Int. Cl.[7] .............................................. G01N 1/10
(52) U.S. Cl. ............................. 73/863.03; 73/863.51; 73/863.81
(58) Field of Search ........................ 73/863.31, 863.33, 73/863.51, 863.52, 863.53, 863.61, 863.81, 73/864.81

(56) References Cited

U.S. PATENT DOCUMENTS

| | | | |
|---|---|---|---|
| 3,842,678 A | | 10/1974 | De Baun et al. |
| 3,930,414 A | | 1/1976 | Russell |
| 4,047,437 A | * | 9/1977 | Brooks .................... 73/863.23 |
| 4,150,574 A | | 4/1979 | Wolf |
| 4,413,533 A | * | 11/1983 | Diesel .................... 73/863.31 |
| 4,442,720 A | * | 4/1984 | Apley et al. ............. 73/863.31 |
| 4,566,342 A | | 1/1986 | Kurz |
| 4,660,587 A | | 4/1987 | Rizzle |
| 4,739,647 A | * | 4/1988 | Monticelli, Jr. .............. 73/23.2 |
| 4,860,598 A | | 8/1989 | Bailey et al. |
| 5,703,299 A | * | 12/1997 | Carleton et al. ......... 73/863.83 |
| 6,241,950 B1 | | 6/2001 | Veelenturf et al. |
| 6,615,679 B1 | * | 9/2003 | Knollenberg et al. .... 73/863.33 |
| 2003/0019304 A1 | | 1/2003 | Taylor et al. |

* cited by examiner

Primary Examiner—Charles Garber
(74) Attorney, Agent, or Firm—Nixon & Vanderhye P.C.

(57) ABSTRACT

A method and system of obtaining a spatially representative sample of fluid flowing through a duct comprises providing a sample probe having a plurality of inlet ports in the duct, controlling a back pressure within the sample probe so that the back pressure within the sample probe at each inlet port is the same, and receiving a sample portion of the fluid into the plurality of inlet ports. The back pressure may be equal to a static pressure of an outlet portion of the duct. The back pressure may be controlled by venting the sample probe to atmosphere, using a pressure regulator connected to the sample probe or venting to an opening in a wall of an outlet portion of the duct. A cross sectional area of the sample probe may be at least ten times larger than a sum of respective cross sectional areas of the inlet ports.

39 Claims, 3 Drawing Sheets

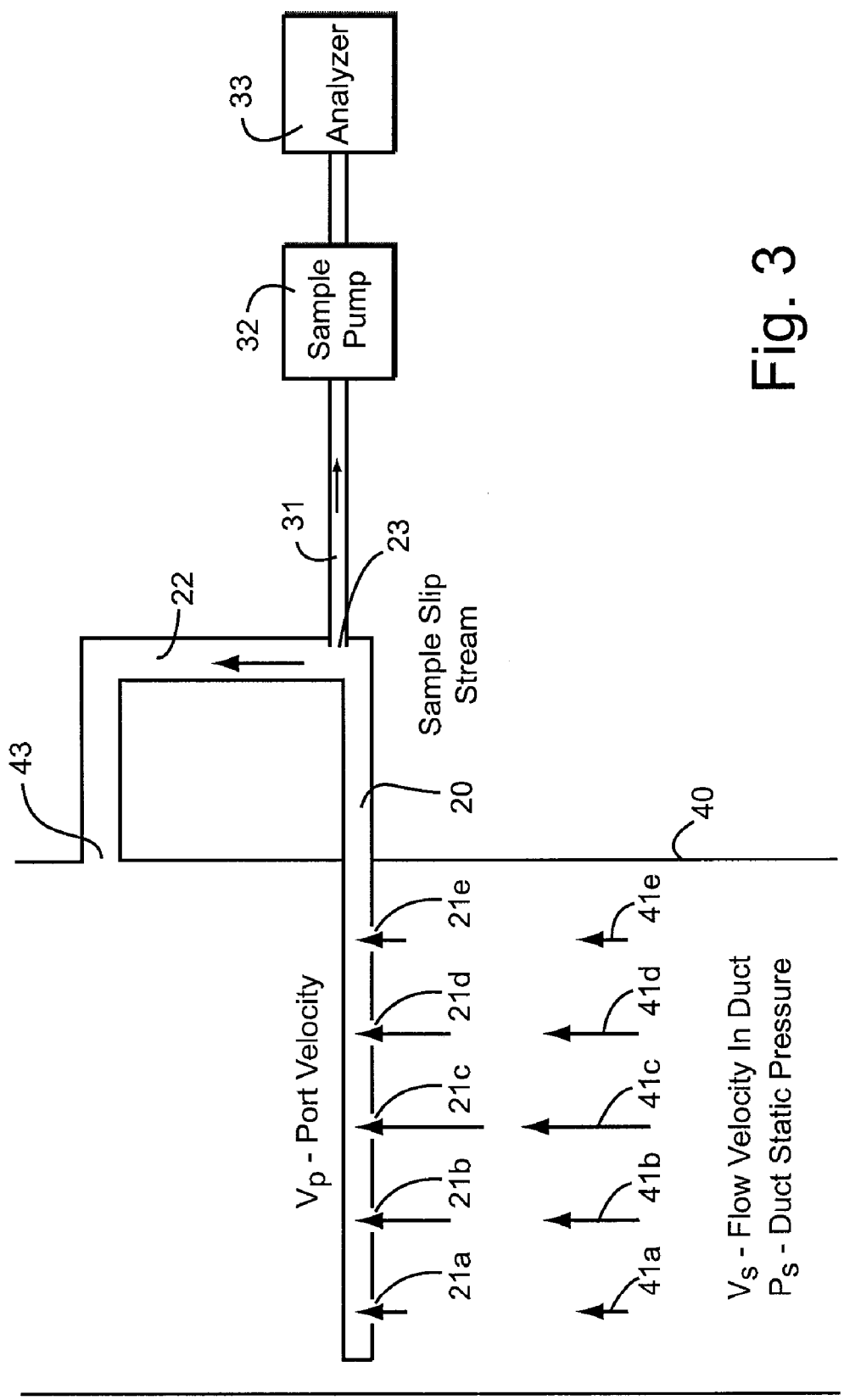

MULTI-POINT SAMPLING METHOD FOR OBTAINING ISOKINETIC FLUID COMPOSITION FLOWS IN A NON-UNIFORM VELOCITY FLOW FIELD

CROSS REFERENCE TO RELATED APPLICATIONS

This application is related to commonly assigned U.S. application Ser. No. 10/605,794 entitled "A Configurable Multi-point Sampling Method and System for Representative Gas Composition Measurements in a Stratified Gas Flow Stream", filed concurrently herewith and naming Neil C. Widmer as inventor, the contents of which are incorporated herein by reference.

BACKGROUND OF INVENTION

The present invention relates to a method and system of obtaining a spatially representative sample of flowing fluid, and particularly relates to a method and system of obtaining an isokinetic sample of flowing fluid utilizing a multi-point sampling probe.

Emissions flowing in an exhaust stack of a gas turbine have been routinely sampled for many years. This sampling may indicate when emissions contain certain concentrations of pollutants. It is thus necessary to ensure that the emissions are sampled accurately.

Non-representative gas sampling in exhaust streams is a significant contributor to inaccurate low level gas species (emissions) measurements. For gas turbine applications, many units are being certified at 9 ppm and even as low as 2 to 3 ppm, all normalized to a diluent level of 15% oxygen. In these applications, the effect of a non-representative oxygen sample being off by 0.5% translates to a 7%–15% bias in NOx emissions depending on the excess oxygen exhaust concentration. Additionally, NOx and other pollutant species like CO and NH3 can be highly stratified resulting in large variations of species concentrations.

A current process to achieve representative sampling of an exhaust stream involves measuring multiple points across the stack. This current process is generally a manual process that is not suitable for continuous monitoring systems. Points sampled depend on test method: for 40 CFR 60, App A, Method 20 (turbines) eight points at the lowest O2 levels are sampled, for RATAs (40 CFR 60, App. B) three points are sampled, and for Part 75 between one and three points are sampled.

While multi-point sampling is widely used to obtain a representative sample of fluid, it typically involves a manual process of inserting a sample probe to various locations in the fluid stream. This sampling process is thus laborious and time consuming as it requires multiple measurements to determine the gas velocity and then full-time attendance of a sample metering pump to draw flow through a port of known area at specific flow rates.

When manually sampling at the various locations in the stream, the gas is extracted at equal gas volumes per point. This approach ensures a volume averaged gas concentration across the flow. Obtaining volume averaged flow requires point information on the gas volume flow rate and temperature and point specific flow rate control.

Simple solutions to achieve multi-point sampling often involve using a single probe with multiple sampling holes spaced along the probe length. However, because it involves a common sample line, this approach does not allow easy and on-line adjustment of the flow rate sampled at each point.

A variation to this solution employs a sample probe with critical pressure drop at the sample probe inlets. A sample pump draws flow into the sample probe inlets at equal volumes independent of the sample probe location. This avoids problems with variation in flow due to pressure drop along the sampling probe, so sampling points further into the flow are equally represented. However, it does not provide an isokentic flow. For example, when sampling in a low flow and high flow region, both points are equally represented. This sampling biases the true impact of the low flow. If the low flow region contained twice as much pollutant concentrations but only half as much flow as the high flow region, then the overall emissions would be overly biased (i.e., biased high). As a quantitative example of this overly biased sampling, suppose a low flow region constituted 25% of the entire exhaust flow and contained 10 ppm of NOx and a high flow region constituted 75% of the entire exhaust flow and contained 5 ppm of NOx. In this quantitative example, the flow averaged emission is OLE_LINK1(25%)(10 ppm NOx)+(75%)(5 ppm NOx) OLE_LINK1=6.25 ppm NOx. However, the sampling system would determine the result as 7.5 ppm NOx via the following calculation: (50%)(10 ppm NOx)+(50%)(5 ppm NOx)=7.5 ppm NOx.

In sampling systems where critical pressure drop is not established at the port inlet, further bias can be introduced due to sample line length and pressure head differences. In these cases, sampling further into a flow stream would have higher line pressure losses and lower sampling rates. Assuming the above quantitative example, if the high flow region was in the center of a stack (i.e., center of the flow) and the low flow region was closer to the wall of the stack, and the high flow region formed 45% of the total flow and the low flow region formed 55% of the total flow due to sample line pressure differences, the determined result would be further biased at 7.75 ppm NOx as calculated as follows: (55%)(10 ppm NOx)+(45%)(5 ppm NOx)=7.75 ppm NOx.

Other systems utilize a sampling grid having multiple sampling probes spatially distributed across the flow field. In these systems, the flow is typically drawn through a common pump and is sequenced to get point-to-point sample concentrations rather than average sample concentrations.

There thus remains a need for a method and system of obtaining a more spatially representative sample through a relatively simple multi-point sampling probe utilizing flow velocity of a fluid flowing through a duct to control proportional sampling rates.

SUMMARY OF INVENTION

In one aspect of the present invention, a method and system of obtaining a spatially representative sample of fluid flowing through a duct comprises: providing a sample probe having a plurality of inlet ports in the duct, controlling a back pressure within the sample probe so that the back pressure within the sample probe at each inlet port is the same, and receiving a sample portion of the fluid into the plurality of inlet ports. The back pressure within the sample probe may be controlled so that it is equal to a static pressure of the outlet portion of the duct. The back pressure within the sample probe may be controlled by venting the sample probe to atmosphere, using a pressure regulator fluidly connected to the sample probe so that the back pressure is equal to static pressure in an outlet portion of the duct, or vented to an opening in a wall of an outlet portion of the duct. A cross sectional area of the sample probe may be at least ten times larger than a sum of respective cross sectional areas of the inlet ports. The method and system may further comprise drawing a sample slip stream of the fluid received by the inlet ports through an opening in the sample probe without substantially changing the back pressure in the sample probe. The back pressure within the sample probe may be controlled to minimize the back pressure so that local duct pressure at each inlet port drives the sample portion of the fluid into the inlet ports. The back pressure within the sample probe may be controlled so that mass flow of the sample portion of fluid received into each of the inlet ports is respectively representative of local mass flow of the fluid at each of the inlet ports.

In another aspect of the present invention, a method and system of obtaining an isokinetic sample of fluid flowing through a duct comprises providing a sample probe having a plurality of inlet ports in the duct, controlling back pressure within the sample probe so that the back pressure and variations of the back pressure within the sample probe are minimized, and receiving an isokinetic sample of the fluid into the plurality of inlet ports so that mass flow of the fluid received into each of the inlet ports is respectively equal to local mass flow of the fluid in the duct at each of the inlet ports. The back pressure within the sample probe may be controlled so that it is equal to a static pressure of an outlet portion of the duct. The back pressure may be controlled by venting the sample probe to atmosphere, using a pressure regulator fluidly connected to the sample probe so that for example the back pressure is equal to static pressure in an outlet portion of the duct, or venting a sample probe to an opening in a wall of an outlet portion of the duct. A cross sectional area of the sample probe may be at least ten times larger than a sum of respective cross sectional areas of the inlet ports. The method and system may further comprise drawing a sample slip stream of the fluid received by the inlet ports through an opening in the sample probe without substantially changing the back pressure in the sample probe.

BRIEF DESCRIPTION OF DRAWINGS

FIG. 3 is a diagram of a fluid sampling and continuous monitoring system for obtaining and analyzing an isokinetic sample of fluid flowing through a duct in accordance with another embodiment of the invention.

DETAILED DESCRIPTION

Figure 1:
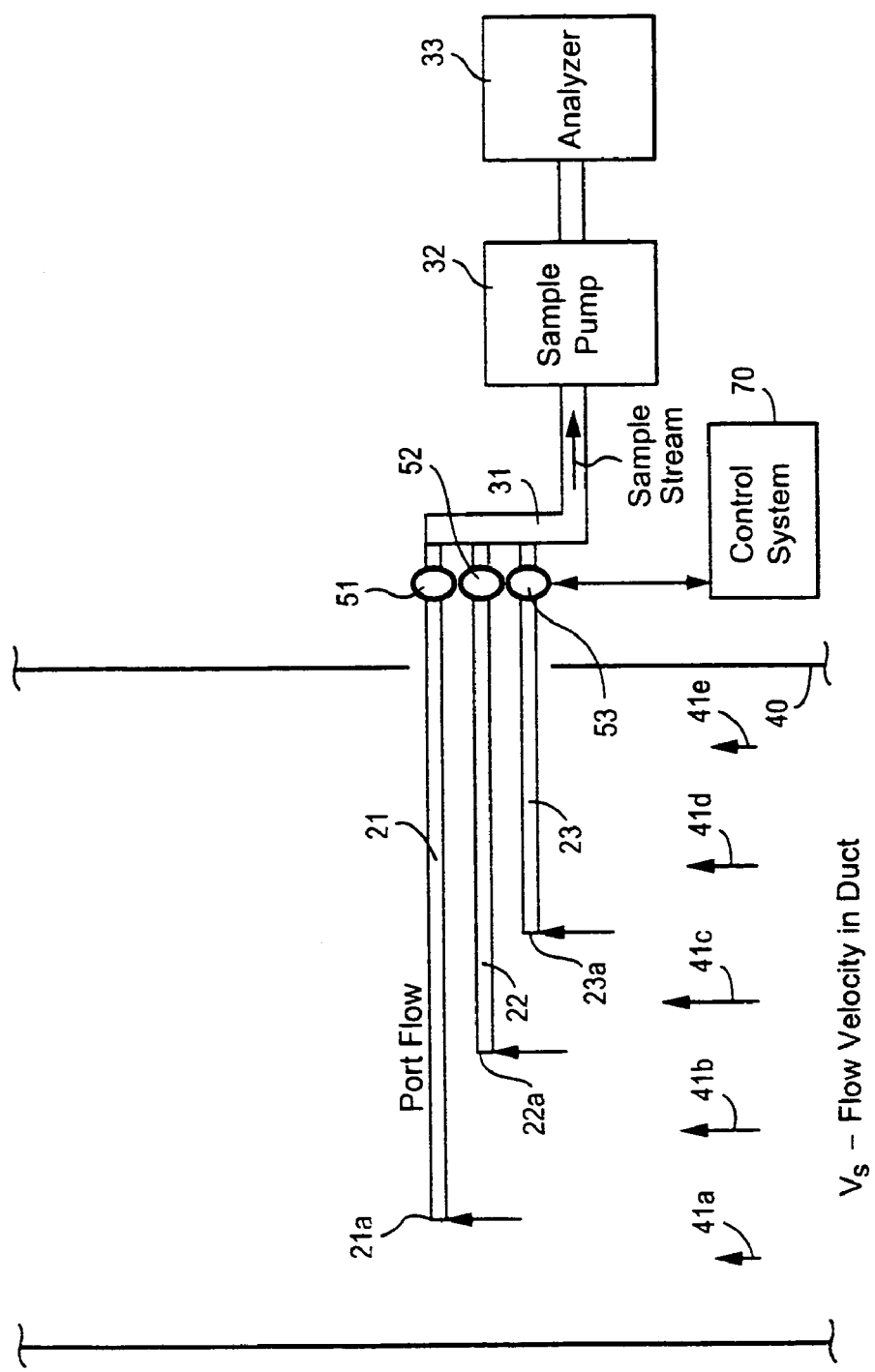
FIG. 1 is a diagram of a fluid sampling and continuous monitoring system for obtaining and analyzing an isokinetic sample of fluid flowing through a duct in accordance with a first embodiment of the invention.

FIG. 1 illustrates an exemplary embodiment of a fluid sampling and continuous monitoring system for obtaining a spatially representative sample of fluid flowing through duct 40. The fluid flowing through duct 40 may be, for example, exhaust gas containing pollutants from a gas turbine. Duct 40 may be, for example, an outlet exhaust stack of the gas turbine.

The system includes a fixed sample probe 20, sample pump 32 and sample analyzer 33. Sample probe 20 is arranged within duct 40 and includes inlet ports 21a–21e, vent portion 22 and opening 23. Sample slip stream passage 31 fluidly connects opening 23 and sample pump 32. Sample analyzer 33 is fluidly connected to sample pump 32.

Sample probe 20 has a uniform cross-sectional area. The cross-sectional area of sample probe 20 is relatively large compared to the cumulative cross-sectional areas of all of the inlet ports 21a–21e. In one exemplary embodiment, the cross-sectional area of sample probe 20 is at least ten times larger than the cumulative total of cross-sectional areas of all of the inlet ports 21a–21e. For example, if the five inlet ports 21a–21e of sample probe 20 each has a diameter of 0.1875 inches, the diameter of sample probe 20 is at least (approximately) 1.3 inches. This (at least) 10:1 cross-sectional area ratio minimizes frictional head losses in sample probe 20 and enables the pressure head to be significantly small so that the sample probe length and cross-sectional area do not form a significant pressure head or pressure variance from one inlet port to another. Impacts of accumulating fluid flow may thus be minimized as a fluid moves down sample probe 20.

Vent portion 22 of sample probe 20 and the outlet portion of duct 40 (top portion of duct 40 illustrated in FIG. 1) are vented to atmosphere. The existing back pressure within the entire sample probe 20 is minimized to atmospheric pressure (Patm—as illustrated in FIG. 1) and matches the static pressure in the outlet portion of duct. The existing back pressure is thus controlled so that it is uniform throughout sample probe 20. In particular, the existing back pressure is uniformly equal to atmospheric pressure in those portions of sample probe 20 where inlet ports 21a–21e are formed. As the back pressure in sample probe 20 becomes ambient (i.e., equal to Patm), the spatial sample representativeness approaches isokinetic.

A gas flows through duct 40 at flow velocity Vs. However, the flow velocity of the gas within different areas of duct 40 is often non-uniform. That is, the flow velocity of the gas has an uneven velocity profile such that local fluid velocities are unequal. One flow velocity profile is graphically illustrated by arrows 41a–41e where larger local flow velocities in duct 40 are illustrated by larger arrows. For example, the local flow velocity in the center of duct 40 is higher (as illustrated by arrow 41c) than the local flow velocities near the walls of duct 40 (as illustrated by arrows 41a and 41e).

Sample probe 20 receives a sample of gas through inlet ports 21a–21e as the gas flows through duct 40. Sample probe 20 uses the fluid stagnation pressure (i.e., the sum of the static pressure Ps in duct 40 and the dynamic pressure in duct 40 resulting from fluid velocity Vs) to obtain an isokinetic sample. Sample probe 20 provides a multi-point sampling without requiring separate pitot probes and temperature measurements and discrete point by point sampling. The sample flow rate in each of inlet ports 21a–21e is proportional to the pressure drop through sampling probe 20.

By utilizing the stagnation pressure to drive the gas sample into inlet ports 21a–21e and minimizing (or eliminating) back pressure in sample probe 20 and pressure variations within sample probe 20, the sample velocity at each inlet port entrance will be approximately equal to the free stream gas velocity at that point. The mass flow into each inlet port is thus representative of the local mass flow of the fluid in duct 40. The total sample will be comprised of sample flow from each region of duct 40 relative to the volume flow rate at that location. As the absolute back pressure approaches ambient (Patm), the sample representativeness will improve and approach isokinetic. The gas flow in sample probe 20 is formed by spatially representative, isokinetic, mass flows from across duct 40. As discussed above, the sum of the cross-sectional areas of all of inlet ports 21a–21e is significantly smaller (e.g., at least ten times smaller) than the sample probe cross sectional area so as to eliminate back pressure and back pressure variations as the sample gas streams contribute to the flow in sample probe 20.

The system can thus obtain a spatially representative sample of gas flowing through duct 40. The flow of sample into each inlet port 21a–21e is controlled by the controlling the back pressure in sample probe 20 to match the static pressure in an outlet portion of duct 40. The flow of sample in each inlet port 21a–21e is at least proportional to the local mass flow at the inlet port and becomes equal to the local mass flow (i.e., isokinetic) if the back pressure is controlled to Patm. Independent port flow controllers are not required. Instead, the fluid's motive force serves as a proportional driver. Representative sampling can therefore be accomplished while avoiding the complexity of performing discrete multi-point sampling.

After a sample of the fluid flowing in duct 40 has been received by inlet ports 21a–21e of sample probe 20, a sample slip stream is drawn through opening 23 by sample pump 32. The sample flow in probe 20 is greater than the sample slip stream so that ambient air is not drawn into sample probe 20. The sample stream therefore does not induce draw of a significant negative pressure so as to upset (i.e., substantially change) the back pressure balance in sample probe 20. Slip stream passage 31 communicates the sample slip stream to sample pump 32. The slip stream sample is then conditioned and analyzed via analyzer 33. For example, an evaluation of NOx and other species (e.g., pollutants) can be conducted utilizing sample analyzer 33 and the optimal points to sample can be assessed based on optimizing O2 corrected species concentration or other criteria as appropriate.

The sampling and continuous monitoring system may be applied, for example, in a continuous emission stack (duct) where stack stratification may be excessive. In particular, the system may be used in gas turbine applications where exhaust particulate matter loadings are low in order to avoid clogging inlet ports 21a–21e or causing variations in size to the inlet ports 21a–21e. Inlet ports 21a–21e may be routinely cleaned so that the system may even be used to sample and monitor "dirty" exhaust streams.

To clean sample probe 20, a high pressure blast of air is supplied to duct 40 to blow out dust and particles. One probe is sufficient to provide 0.5 lpm of sample gas in a 10 ft/s velocity. Calibration of the sampling system can be accomplished by supplying calibration gas to sample probe 20 in a downstream portion of duct 40. Sufficient calibration gas must be supplied for the sample pump demand plus additional flow to ensure flow downstream of duct 40 is reversed.

Figure 2:
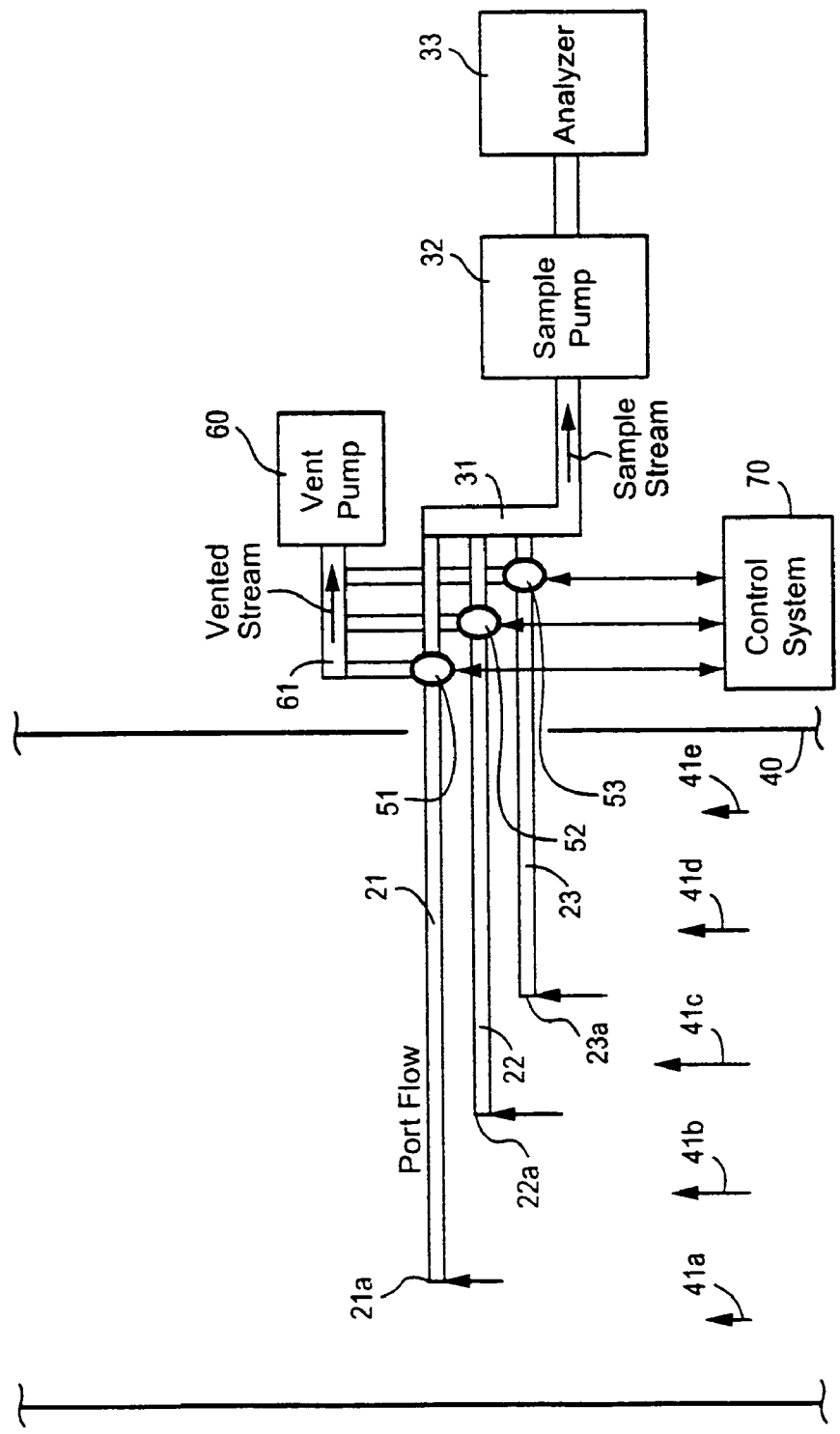
FIG. 2 is a diagram of a fluid sampling and continuous monitoring system for obtaining and analyzing an isokinetic sample of fluid flowing through a duct in accordance with another embodiment of the invention.

FIG. 2 illustrates another exemplary embodiment of a fluid sampling and monitoring system for obtaining a spatially representative sample of a fluid, where identical reference numbers refer to parts common to previous embodiment(s). Only the differences from previous embodiment(s) will be discussed in detail.

The system illustrated in FIG. 2 includes a sample probe 20 having a vent portion 22. Instead of venting vent portion 22 directly to atmosphere, vent portion 22 is connected to a pressure regulator 50. Pressure regulator 50 controls the back pressure within the entirety of sample probe 20 to an optimum level. For example, pressure regulator 50 controls the back pressure so that it is zero relative to ambient pressure throughout the entire sample probe 20 including at those portions of sample probe 20 forming port inlets 21a–21e. As another example, if the outlet portion of duct 40 is connected to a device such as a boiler rather than being vented to atmosphere so that the static pressure in the outlet portion of duct 40 is equal to P1 (see FIG. 2), pressure regulator 50 controls the back pressure within sample probe 20 so that the back pressure in the entire sample probe 20 is also equal to pressure P1. A spatially representative sample (e.g., isokinetic sample) can be obtained as the flow velocity in each inlet port 21a–21e is proportional to (e.g., approximately equal to) the free stream gas velocity at that point and thus the total sample will be comprised of the sample flow from each region of duct 40 relative to the local volume flow rate at that location.

FIG. 3 illustrates another exemplary embodiment of a fluid sampling system for obtaining a spatially representative sample of a fluid, where identical reference numbers refer to parts common to previous embodiments and only the differences from previous embodiments will be discussed in detail. The fluid sampling system illustrated in FIG. 3 includes a sample probe 20 having a vent portion 22. An opening 43 is defined in an outlet portion of duct 40. Vent portion 22 is vented to an outlet portion of duct 40 via opening 43. The back pressure within sample probe 20 will thus match the static pressure in the outlet portion of duct 40. If the back pressure is minimized or eliminated, the sample velocity at each inlet port entrance will be approximately equal to the free stream gas velocity at that point. An isokentic sample of the flowing fluid can thus be obtained.

Rather than using a single probe as illustrated in FIGS. 1–3, a sampling system can include multiple probes. The multiple probes can be spatially orientated in a non-uniform velocity flow profile and the individual sample streams when combined will comprise a spatial and volumetrically representative sample. This avoids the need to measure gas velocity and control the sampling volume flow rate at each point in the duct when sampling isokinetically. An individual sample probe would be used for each sample port inlet location. The outlet gas from each individual sample probe can be connected to a common manifold and mixed to create a well-mixed sample prior to being analyzed by an analyzer.

Single sample probe 20 could also benefit from a manifold and mixing system. In this alternative embodiment, sample pump 32 draws flow from the manifold for subsequent conditioning and analysis by analzyer 33. The sample pump flow rate can be set to extract only a portion of the flow and to balance the manifold pressure at zero or slightly positive. Any excess flow returns out vent portion 22. To accomplish back pressure control, vent portion 22 can be vented to atmosphere or to a down-stream duct location (static pressure location), but the flow must be unidirectional. A directional flow indicator on the static port outlet can insure the pump sampling rate is not excessive and not drawing flow backwards.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. A method of obtaining a spatially representative, isokinetic, sample of fluid flowing through a duct, the method comprising:

providing a sample probe having a plurality of inlet ports in the duct without respective flow controllers coupled to each of the inlet ports for controlling fluid flow therethrough;

controlling a back pressure within the sample probe so that the back pressure within the sample probe at each inlet port is the same and so that the back pressure within the sample probe is equal to a static pressure of an outlet portion of the duct; and receiving an isokinetic sample portion of the fluid into the plurality of inlet ports so that mass flow of the sample portion of fluid received into each of the inlet ports without respective flow controllers is respectively representative of local mass flow of the fluid at each of the inlet ports.

2. A method of claim 1 wherein the back pressure within the sample probe is controlled by venting the sample probe to atmosphere.

3. A method of claim 1 wherein the back pressure within the sample probe is controlled using a pressure regulator fluidly connected to the sample probe.

4. A method of claim 1 wherein the sample probe is vented to an opening in a wall of an outlet portion of the duct.

5. A method of claim 1 wherein a cross sectional area of the sample probe is at least ten times larger than a sum of respective cross sectional areas of the inlet ports.

6. A method of claim 1 further comprising drawing a sample slip stream of the fluid received by the inlet ports through an opening in the sample probe without substantially changing the back pressure in the sample probe.

7. A method of claim 1 wherein controlling the back pressure within the sample probe comprises minimizing the back pressure so that local duct pressure at each inlet port drives the sample portion of the fluid into the inlet ports.

8. A method of obtaining an isokinetic sample of fluid flowing through a duct, the method comprising:

providing a sample probe having a plurality of inlet ports in the duct without respective flow controllers coupled to each of the inlet ports for controlling fluid flow therethrough;

controlling a back pressure within the sample probe so that the back pressure and variations of the back pressure within the sample probe are minimized and so that the back pressure within the sample probe is equal to a static pressure of an outlet portion of the duct; and receiving an isokinetic sample of the fluid into the plurality of inlet ports so that mass flow of the fluid received into each of the inlet ports without respective flow controllers is respectively equal to local mass flow of the fluid in the duct at each of the inlet ports.

9. A method of claim 8 wherein the back pressure within the sample probe is controlled by venting the sample probe to atmosphere.

10. A method of claim 8 wherein the back pressure within the sample probe is controlled using a pressure regulator connected to the sample probe.

11. A method of claim 8 wherein the sample probe is vented to an opening in a wall of an outlet portion of the duct.

12. A method of claim 8 wherein a cross sectional area of the sample probe is at least ten times larger than a sum of respective cross sectional areas of the inlet ports.

13. A method of claim 8 further comprising drawing a sample slip stream of the fluid received by the inlet ports through an opening in the sample probe without substantially changing the back pressure in the sample probe.

14. A system for obtaining a spatially representative, isokinetic, sample of fluid flowing through a duct, the system comprising:

a sample probe having a plurality of inlet ports in the duct without respective flow controllers coupled to each of the inlet ports for controlling fluid flow therethrough, a back pressure within the sample probe being controlled so that the back pressure within the sample probe at each inlet port is the same and so that the back pressure within the sample probe is equal to a static pressure of an outlet portion of the duct, and an isokinetic sample portion of the fluid being received into the plurality of inlet ports so that mass flow of the sample portion of fluid received into each of the inlet ports without respective flow controllers is respectively representative of local mass flow of the fluid at each of the inlet ports.

15. A system of claim 14 wherein the back pressure within the sample probe is controlled by venting the sample probe to atmosphere.

16. A system of claim 14 further comprising a pressure regulator for controlling the back pressure within the sample probe, the pressure regulator being fluidly connected to the sample probe.

17. A system of claim 14 wherein the sample probe is vented to an opening in a wall of an outlet portion of the duct.

18. A system of claim 14 wherein a cross sectional area of the sample probe is at least ten times larger than a sum of respective cross sectional areas of the inlet ports.

19. A system of claim 14 wherein a sample slip stream of the fluid received by the inlet ports is drawn through an opening in the sample probe without substantially changing the back pressure in the sample probe.

20. A system of claim 14 wherein controlling the back pressure within the sample probe comprises minimizing the back pressure so that local duct pressure at each inlet port drives the sample portion of the fluid into the inlet ports.

21. A system of obtaining an isokinetic sample of fluid flowing through a duct, the system comprising:

a sample probe having a plurality of inlet ports in the duct without respective flow controllers coupled to each of the inlet ports for controlling fluid flow therethrough, a back pressure within the sample probe being controlled so that the back pressure and variations of the back pressure within the sample probe are minimized and so that the back pressure within the sample probe is equal to a static pressure of an outlet portion of the duct, and an isokinetic sample of the fluid being received into the plurality of inlet ports so that mass flow of the fluid received into each of the inlet ports without respective flow controllers is respectively equal to local mass flow of the fluid in the duct at each of the inlet ports.

22. A system of claim 21 wherein the back pressure within the sample probe is controlled by venting the sample probe to atmosphere.

23. A system of claim 21 further comprising a pressure regulator for controlling the back pressure within the sample probe, the pressure regulator being connected to the sample probe.

24. A system of claim 21 wherein the sample probe is vented to an opening in a wall of an outlet portion of the duct.

25. A system of claim 21 wherein a cross sectional area of the sample probe is at least ten times larger than a sum of respective cross sectional areas of the inlet ports.

26. A system of claim 21 wherein a sample slip stream of the fluid received by the inlet ports is drawn through an opening in the sample probe without substantially changing the back pressure in the sample probe.

27. A system for obtaining a spatially representative, isokinetic, sample of fluid flowing through a duct, the system comprising:

means for sampling fluid in the duct, the means for sampling fluid having a plurality of inlet ports for receiving a sample portion of the fluid without respective flow controllers coupled to each of the inlet ports for controlling fluid flow therethrough so that mass flow of the sample portion of fluid received into each of the inlet ports without respective flow controllers is respectively representative of local mass flow of the fluid at each of the inlet ports; and means for controlling a back pressure within the means for sampling so that the back pressure within the means for sampling at each inlet port is the same and so that the back pressure within the means for sampling is equal to a static pressure of an outlet portion of the duct.

28. A system of claim 27 wherein the means for controlling the back pressure controls the back pressure within the means for sampling by venting the means for sampling to atmosphere.

29. A system of claim 27 wherein the means for controlling back pressure includes a pressure regulator which is fluidly connected to the means for sampling.

30. A system of claim 27 wherein the means for sampling is vented to an opening in a wall of an outlet portion of the duct.

31. A system of claim 27 wherein a cross sectional area of the means for sampling is at least ten times larger than a sum of respective cross sectional areas of the inlet ports.

32. A system of claim 27 wherein a sample slip stream of the fluid received by the inlet ports is drawn through an opening in the means for sampling without substantially changing the back pressure in the means for sampling.

33. A system of claim 27 wherein controlling the back pressure within the means for sampling by the means for controlling comprises minimizing the back pressure so that local duct pressure at each inlet port drives the sample portion of the fluid into the inlet ports.

34. A system obtaining an isokinetic sample of fluid flowing through a duct, the system comprising:

means for sampling fluid in the duct, the means for sampling having a plurality of inlet ports without respective flow controllers coupled to each of the inlet ports for controlling fluid flow therethrough, the inlet ports receiving an isokinetic sample of the fluid so that mass flow of the fluid received into each of the inlet ports is respectively equal to local mass flow of the fluid in the duct at each of the inlet ports; and means for controlling a back pressure within the means for sampling so that the back pressure and variations of the back pressure within the means for sampling are minimized and so that the back pressure within the means for sampling is equal to a static pressure of an outlet portion of the duct.

35. A system of claim 34 wherein the means for controlling the back pressure controls the back pressure by venting the means for sampling to atmosphere.

36. A system of claim 34 wherein the means for controlling the back pressure includes a pressure regulator which is connected to the means for sampling.

37. A system of claim 34 wherein the means for sampling is vented to an opening in a wall of an outlet portion of the duct.

38. A system of claim 34 wherein a cross sectional area of the means for sampling is at least ten times larger than a sum of respective cross sectional areas of the inlet ports.

39. A system of claim 34 wherein a sample slip stream of the fluid received by the inlet ports is drawn through an opening in the means for sampling without substantially changing the back pressure in the means for sampling.

* * * * *